(12) United States Patent
Asano et al.

(10) Patent No.: US 8,008,610 B2
(45) Date of Patent: Aug. 30, 2011

(54) ILLUMINATION LIGHT QUANTITY SETTING METHOD IN IMAGE MEASURING INSTRUMENT

(75) Inventors: Hidemitsu Asano, Kawasaki (JP); Sadayuki Matsumiya, Kawasaki (JP)

(73) Assignee: Mitutoyo Corporation, Kawasaki-shi (JP)

( * ) Notice: Subject to any disclaimer, the term of this patent is extended or adjusted under 35 U.S.C. 154(b) by 53 days.

(21) Appl. No.: 12/318,127

(22) Filed: Dec. 22, 2008

(65) Prior Publication Data

US 2009/0180708 A1  Jul. 16, 2009

(30) Foreign Application Priority Data

Jan. 11, 2008 (JP) ................................. 2008-004650

(51) Int. Cl.
*G01J 1/32* (2006.01)

(52) U.S. Cl. ...................................................... 250/205
(58) Field of Classification Search .................. 250/205; 362/5

See application file for complete search history.

(56) References Cited

U.S. PATENT DOCUMENTS

| | | | |
|---|---|---|---|
| 2002/0134910 A1 | 9/2002 | Kokubu et al. | |
| 2007/0206183 A1 | 9/2007 | Lebens | |
| 2008/0151194 A1* | 6/2008 | Segev | 353/28 |

FOREIGN PATENT DOCUMENTS

| | | |
|---|---|---|
| JP | A-51-56253 | 5/1976 |
| JP | A-09-304034 | 11/1997 |
| JP | A-2001-041710 | 2/2001 |
| JP | A-2003-269919 | 9/2003 |
| JP | A-2006-126200 | 5/2006 |

\* cited by examiner

*Primary Examiner* — Thanh X Luu
(74) *Attorney, Agent, or Firm* — Oliff & Berridge, PLC

(57) ABSTRACT

An image measuring instrument includes a camera that images a plurality of measured points based on a preset measuring procedure, and an illumination unit that irradiates the measured points. The image measuring instrument measures a dimension and a shape of a to-be-measured object while the illumination unit irradiates light having illumination light quantity corresponding to an illumination preset value with reference to the illumination preset value that is preliminarily set for every measured point. An illumination light quantity setting method includes a command signal output step that outputs a command signal for irradiating light having the illumination light quantity corresponding to the illumination preset value for every measured point, an offset value assigning step that assigns an offset value to the command signal to be sent to the illumination unit, and a setting step that sets the offset value to be variable.

5 Claims, 5 Drawing Sheets

100 # ILLUMINATION LIGHT QUANTITY SETTING METHOD IN IMAGE MEASURING INSTRUMENT

BACKGROUND OF THE INVENTION

1. Field of the Invention

The present invention relates to an illumination light quantity setting method in an image measuring instrument, and particularly to an illumination light quantity setting method in an image measuring instrument including an image pickup for imaging a plurality of measured points based on a preset measuring procedure and an illuminator for irradiating the measured points to measure a dimension and a shape of an object to be measured.

2. Description of Related Art

A conventional image measuring instrument has been used to measure a surface texture of an object to be measured by applying an image processing to an image of the object to be measured, the image being captured by an image pickup. It is important for the image measuring instrument that an illumination condition (an illumination preset value) is set to enhance contrast of the captured image so that an edge position of the object to be measured is reliably and accurately detected.

In such image measuring instrument, a system for optimally setting an illumination condition when detecting an edge position has been known (for example, see Document 1: JP-A-09-304034 (FIG. 3)).

In the image measuring instrument disclosed in Document 1, light quantity is initially changed by several pitches at every predetermined measured point in order to preliminarily set optimal light quantity at the measured point, and then a contrast value on an image at the measured point is calculated at every change of light quantity. Subsequently, an illumination light quantity having the highest contrast value is calculated as an illumination preset value by applying the contrast value and illumination light quantity to a quadratic function. The calculated illumination preset value is set for every measured point to be stored in a work memory or the like.

The image measuring instrument images the plurality of measured points with light having illumination quantity of the optimal illumination preset value with reference to the stored illumination preset values. The image measuring instrument stores a part program that sequentially measures the plurality of measured points in accordance with a preset measuring procedure. By executing the part program, a plurality of objects to be measured having the same shape can be efficiently and repeatedly measured.

However, in the image measuring instrument disclosed in Document 1, when actual quantity of light irradiated from an illumination light source is changed, such as when the illumination light source (illuminator) deteriorates with the passage of time or when the illumination light source is replaced, it is necessary that the illumination preset values in the part program are modified for all of the measured points. This modification has been effort-consuming.

SUMMARY OF THE INVENTION

An object of the invention is to provide an illumination light quantity setting method capable of easily setting the same illumination quantity without modifying an illumination preset value that is set for every measured point when light quantity of an illuminator is changed in an image measuring instrument.

According to an aspect of the invention, an illumination light quantity setting method in an image measuring instrument including an image pickup that images a plurality of measured points based on a preset measuring procedure and an illuminator that irradiates the measured points with light having illumination light quantity corresponding to a provided command signal, the image measuring instrument measuring a dimension and a shape of a to-be-measured object while the illuminator irradiates the measured points with light having illumination light quantity corresponding to an illumination preset value with reference to the illumination preset value that is preliminarily set and stored for each of the measured points, the setting method includes: a command signal output step that outputs the command signal for irradiating light having the illumination light quantity corresponding to the illumination preset value for each of the measured points; an offset value assigning step that assigns an offset value to the command signal to be sent to the illuminator; and a setting step that sets the offset value to be variable.

According to the aspect of the invention, the command signal based on the preset illumination preset value that is preliminarily set for every measured point is initially sent to the illuminator in the command signal output step. Then, the offset value is assigned to the sent command signal in the offset value assigning step. Subsequently, the illuminator receives the command signal assigned with the offset value to irradiate the measured point with light having the predetermined illumination light quantity. In the setting step, for example, when a state of the illuminator is changed, the offset value is set so that quantity of illumination light irradiated from the illuminator on the receipt of the command signal based on the same illumination preset value remains the same before and after the change of the state of the illuminator. As described above, quantity of illumination light irradiating the measured point is set.

Thus, when the illumination light quantity of the illuminator is changed, such as when the illuminator deteriorates with the passage of time or when the illuminator is replaced, an initial value of the illumination light quantity can be maintained only by setting the offset value without modifying the illumination preset value for every measured point.

For example, the assigned offset value may be changed in accordance with the duration of use of the illuminator. At this time, the offset value decided according to the duration of use may be inputted. Alternatively, offset values according to durations of use may be preliminary stored so that an offset value is automatically updated according to the duration of use.

Also, when the illuminator is replaced, for example, only an offset value may be set in accordance with a changing amount of illumination light quantity before and after the replacement, so that it is not necessary to individually modify the illumination preset value that is set for every measured point.

In the setting step in the illumination light quantity setting method in the image measuring instrument according to the aspect of the invention, a reference brightness information of the illumination light irradiated from the illuminator corresponding to the command signal may be detected and stored. After the reference brightness information is detected, a brightness information of the illumination light irradiated from the illuminator corresponding to the command signal may be detected to be compared with the reference brightness information, and the offset value may be changed when a variation of the brightness information relative to the reference brightness information is out of a predetermined range.

The brightness information may be acquired, for example, by image processing of image data of the measured point captured by the image pickup.

According to the aspect of the invention, after the reference brightness information of illumination light irradiating the predetermined measured point is detected to be stored, the brightness information of the illumination light irradiating the same measured point is detected to be compared with the reference brightness information in order to judge whether a changing amount of the brightness information is out of the predetermined range. When the changing amount is out of the predetermined range, an offset value is changed so that the changing amount of the brightness information is within the predetermined range to obtain a desired offset value. Thus, for example, only by setting a threshold for judging a changing amount, a program can be established to automatically set an offset value in the above-described method, which allows easy setting of an offset value.

In the setting step in the illumination light quantity setting method according to the aspect of the invention, the brightness information of the illumination light irradiating the reference gauge may be detected.

According to such setting method, due to the reference gauge, the brightness information of illumination light can be accurately detected as compared with an arrangement in which brightness information of a measured point of any object to be measured. Thus, a changing amount of quantity of illumination light actually irradiating from the illuminator can be smaller.

An image measuring instrument according to another aspect of the invention includes an image pickup that images a plurality of measured points based on a preset measuring procedure, and an illuminator that irradiates the measured points with light having illumination light quantity in accordance with a provided command signal, and measures a dimension and a shape of a to-be-measured object while the illuminator irradiates the measured points with light having illumination light quantity corresponding to an illumination preset value with reference to the illumination preset value that is preliminary set and stored for each of the measured points. The image measuring instrument includes: a command signal output unit that outputs a command signal for irradiating light having the illumination light quantity corresponding to the illumination preset value for each of the measured points; an offset value assigning unit that assigns an offset value to the command signal to be sent to the illuminator; and a setting unit that sets the offset value to be variable.

With such arrangement, the same advantages as those of the above-described aspect of the invention can be attained. Specifically, when light quantity of the illuminator is changed, the illumination light quantity can be easily set to be the same without modifying the illumination preset value that is preliminarily set for every measured point.

DETAILED DESCRIPTION OF PREFERRED EMBODIMENT(S)

An exemplary embodiment of the invention will be described below with reference to the accompanying drawings.

Explanation of Overall Arrangement

Figure 1:
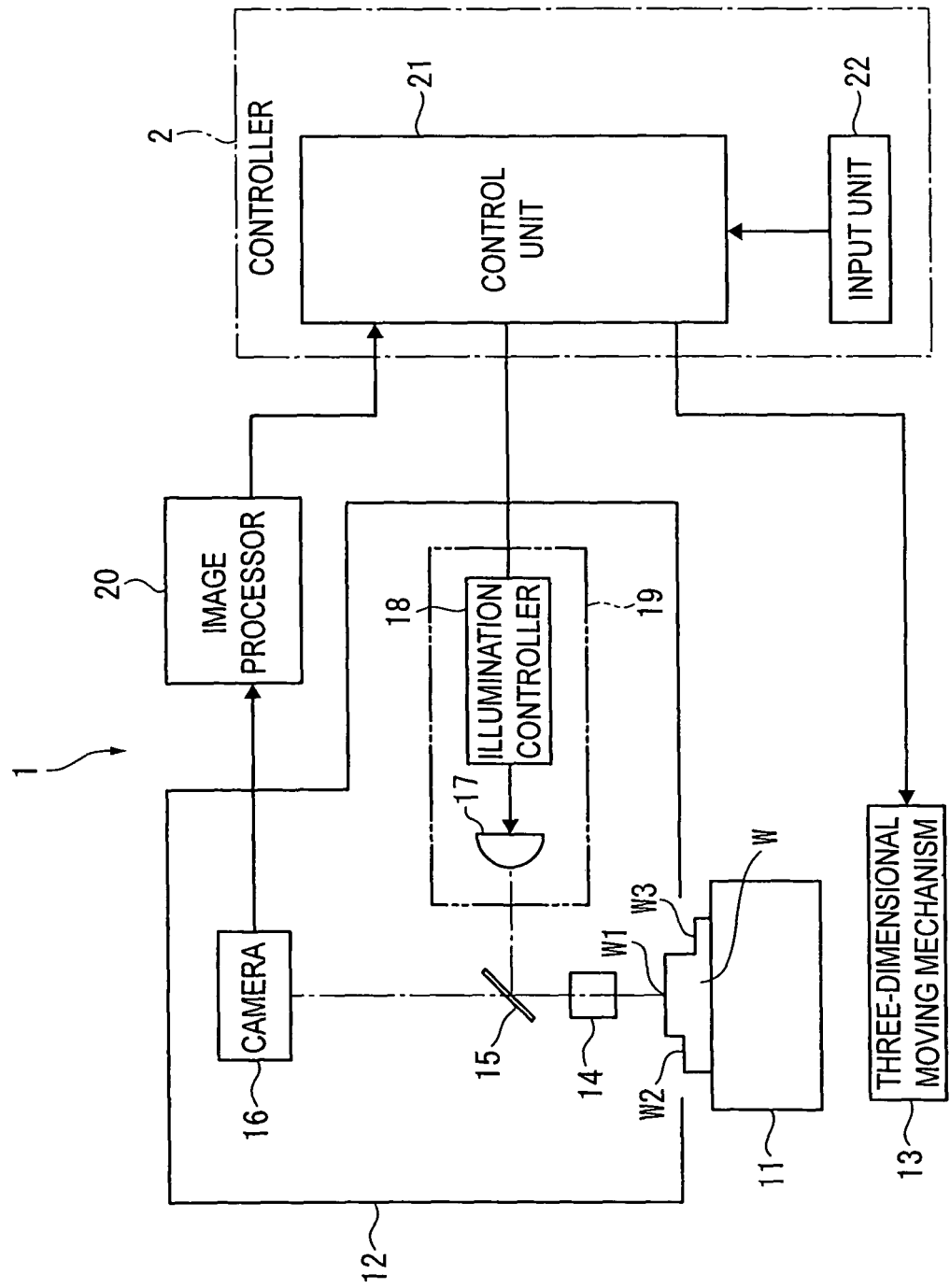
FIG. 1 is a block diagram illustrating an overall arrangement of an image measuring instrument according to an exemplary embodiment of the invention.

FIG. 1 illustrates an exemplary embodiment of an image measuring instrument applied to a measuring method of the invention. The image measuring instrument includes an image data acquiring device 1 for acquiring image data of a to-be-measured object W, and a controller 2 for controlling the image data acquiring device 1 while obtaining a dimension and a shape of the to-be-measured object W from the image data acquired by the image data acquiring device 1.

The image data acquiring device 1 includes a stage 11, a body 12 provided relatively movable in three-dimensional directions relative to the stage 11, and a three-dimensional moving mechanism 13 for relatively moving the stage 11 and the body 12 in the three-dimensional directions.

The to-be-measured object W is mounted on an upper surface of the stage 11. Three measured points W1, W2, and W3 are set on the to-be-measured object W.

In the body 12, an objective lens 14, a beam splitter 15, and a camera 16 are arranged in order immediately above the to-be-measured object W while an epi-illumination light source 17 (hereinafter referred to as a light source 17) is provided for irradiating light from immediately above the to-be-measured object W through the beam splitter 15.

The light source 17 is controlled by an illumination controller 18 to irradiate the measured points W1, W2, and W3 with light having a predetermined illumination light quantity. The light source 17 and the illumination controller 18 define an illumination unit 19 in the form of an illuminator.

The camera 16 in the form of an image pickup captures the measured points W1 to W3 in a preset measuring procedure to send the captured image data of the to-be-measured object W to an image processor 20. The image data is subjected to an image processing in the image processor 20 and subsequently is sent to the controller 2.

The three-dimensional moving mechanism 13 relatively moves the stage 11 and the body 12 in three-dimensional directions (X, Y, and Z directions). For example, the three-dimensional moving mechanism 13 moves the stage 11 in a front-and-rear direction (Y direction) and moves the body 12 in a right-and-left direction (X direction) and in an up-and-down direction (Z direction). Incidentally, it should be noted that an arrangement of the three-dimensional moving mechanism 13 is not limited thereto. Though not illustrated, displacement detectors are provided to detect an amount of displacement in the X, Y and Z directions, respectively. The respective detected amounts of displacements in the X, Y and Z directions are sent to the controller 2.

The controller 2 includes a control unit 21 and an input unit 22. The control unit 21 drives the three-dimensional moving mechanism 13 in accordance with a preset program while controlling the light source 17 via the illumination controller 18. The control unit 21 also calculates a dimension and a shape of the to-be-measured object W from the image data processed in the image processor 20. The input unit 22 is provided to input measuring conditions, data of an object to be measured, or the like.

Explanation of Control Unit 21

Figure 2:
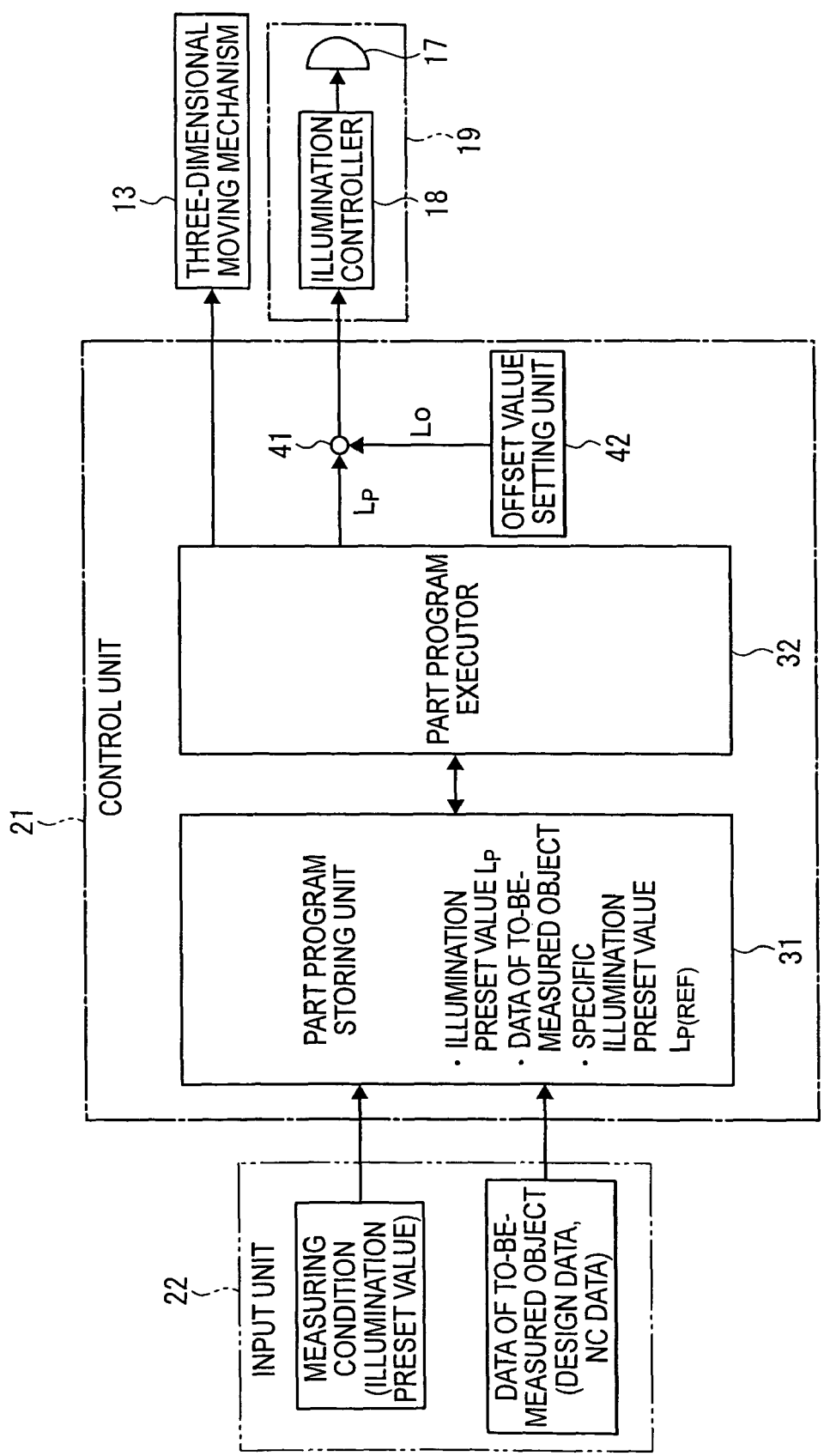
FIG. 2 is a block diagram illustrating a control unit of the image measuring instrument.

FIG. 2 illustrates an arrangement of the control unit 21.

The control unit 21 includes a part program storing unit 31, a part program executor 32, an offset value assigner 41, and an offset value setting unit 42.

The part program storing unit 31 stores the measuring conditions (illumination preset value $L_p$) inputted from the input unit 22, data of an object to be measured (such as design data, NC data or the like), and a part program. The part program is described in a programming language to execute a predetermined measuring procedure with reference to the stored conditions and data. Due to the part program, images of the measured points W1 to W3 of the to-be-measured object W are taken in by using the objective lens 14 and the camera 16 in the predetermined measuring procedure, so that a dimension and a shape of the to-be-measured object W are measured from the image data. A plurality of to-be-measured objects W can be repeatedly measured.

The part program storing unit 31 stores a specific illumination preset value $L_p$(REF) as one of measuring conditions. The specific illumination preset value $L_p$(REF) is an illumination preset value which is set when a reference gauge is to be measured in place of a to-be-measured object W. For example, the specific illumination preset value $L_p$(REF) is used to initially set the light source 17 when an image measuring instrument is newly provided.

The part program executer 32 executes processing in accordance with a later-described flow chart shown in FIG. 4 when the part program starts. The part program executer 32 sends a command signal based on an illumination preset value $L_p$ which is set for each point of the measured points W1 to W3. Accordingly, the part program executer 32 defines a command signal output unit of the invention.

The offset value assigner 41 in the form of an offset value assigning unit assigns an offset value $L_0$ stored in the offset value setting unit 42 with the command signal sent from the part program executer 32 to the illumination controller 18.

Explanation of Offset Value Setting Unit 42

Figure 3:
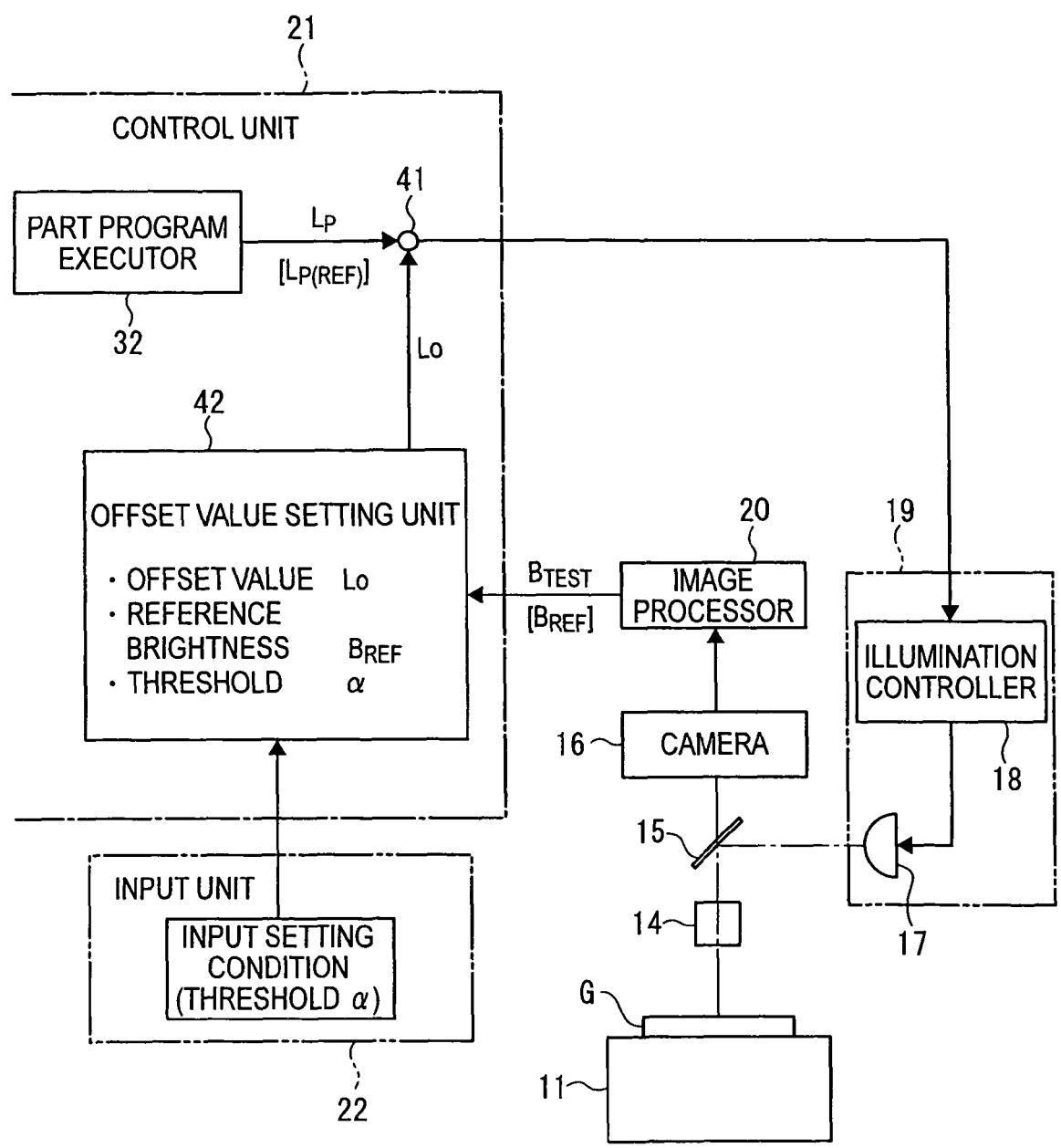
FIG. 3 is a block diagram illustrating an arrangement of an offset value setting unit of the image measuring instrument.

FIG. 3 illustrates an arrangement of the offset value setting unit 42.

The offset value setting unit 42 stores the offset value $L_0$. An initial value of the offset value $L_0$ is 0. In the offset value setting unit 42, a brightness information B included in the image data from the image processor 20 is inputted. The brightness information B includes a reference brightness $B_{REF}$ and a test brightness $B_{TEST}$. The reference brightness $B_{REF}$ is the brightness information B at the time of measurement by using a reference gauge G when an image measuring instrument is initially installed while the test brightness $B_{TEST}$ is the brightness information B at the time of regular measurement by using the reference gauge G after using the image measuring instrument. The reference brightness $B_{REF}$ is stored in the offset value setting unit 42.

Also, a threshold α is inputted as a setting condition by the input unit 22 and stored in the offset value setting unit 42.

The offset value setting unit 42 regularly executes setting processing of the offset value $L_0$ in accordance with a later-described flow chart shown in FIG. 5 to allow the offset value $L_0$ to be variable.

Explanation of Illumination Light Quantity Setting Method

Figure 4:
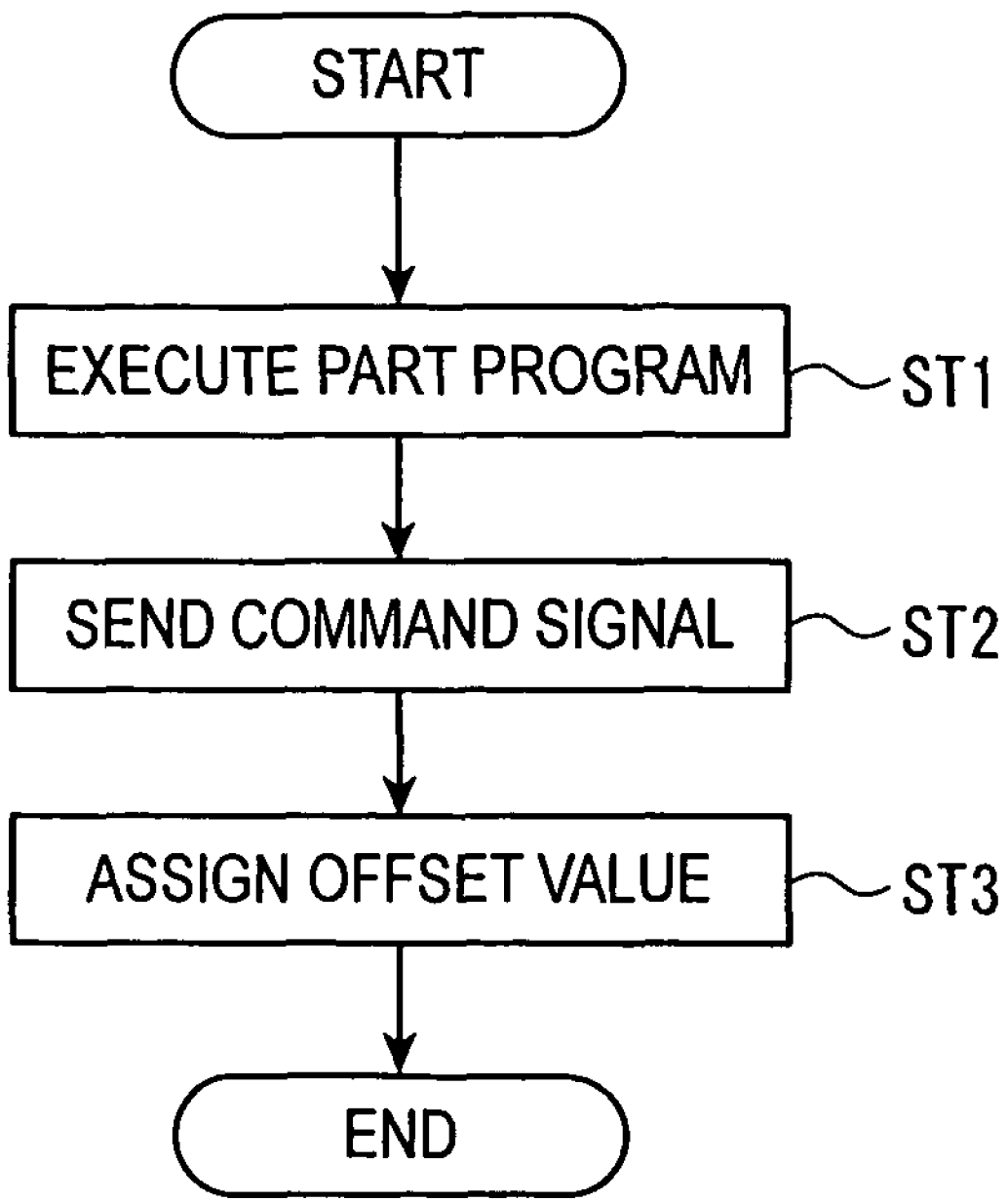
FIG. 4 is a flow chart illustrating an illumination light quantity setting method of the image measuring instrument.

Illumination light quantity is set in ST1 to ST3 as shown in FIG. 4.

In a part program executing step (hereinafter referred to as ST1), the part program storing unit 31 is read to execute the part program.

In a command signal output step (hereinafter referred to as ST2), the command signal based on the illumination preset value $L_p$ for each of the measured points W1 to W3 is sent to the illumination controller 18.

In a offset value assigning step (hereinafter referred to as ST3), an offset value $L_0$ is assigned to the sent command signal. The illumination controller 18 receives the command signal assigned with the offset value $L_0$ and irradiates the light source 17 with light having a predetermined illumination light quantity.

Incidentally, the command signal is sent for each of the measured points W1 to W3, and processing in ST2 and ST3 are executed every time the command signal is sent.

Quantity of illumination light to actually irradiate the measured points W1 to W3 from the light source 17 is set as described above.

Explanation of Offset Value $L_0$ Setting Method

Figure 5:
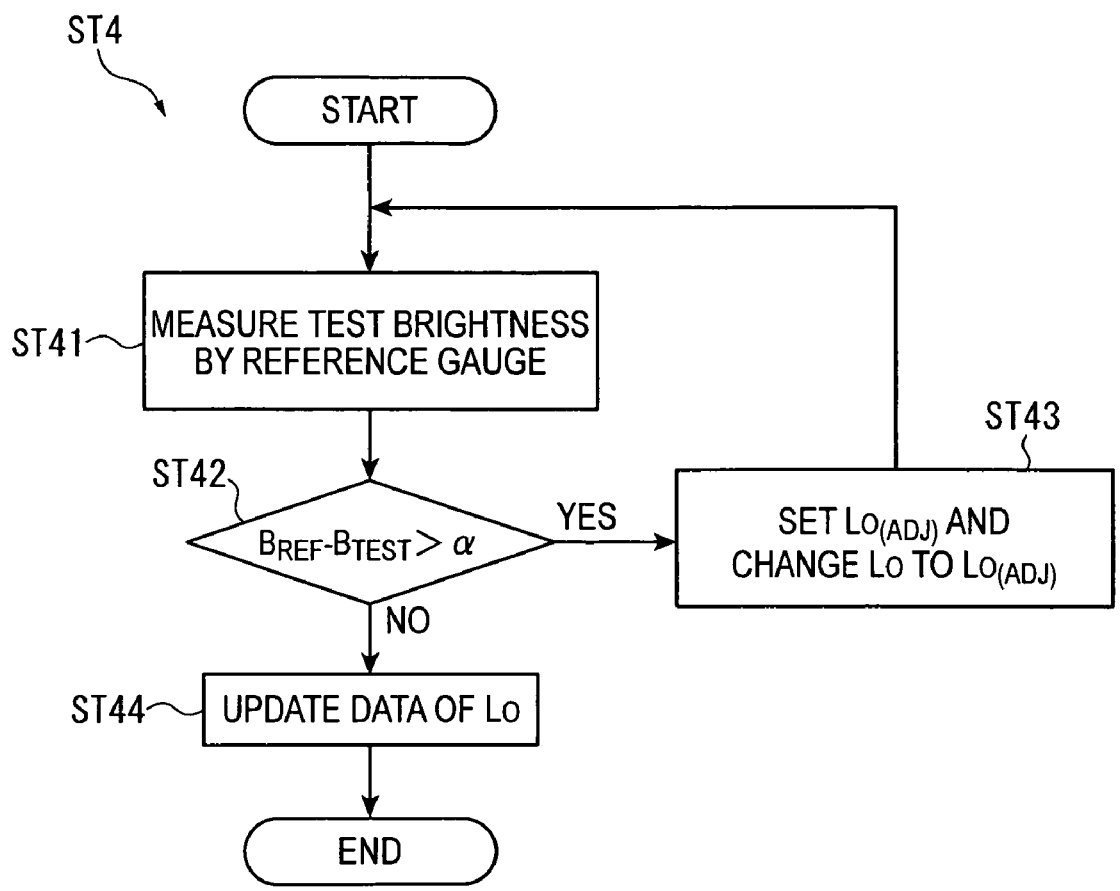
FIG. 5 is a flow chart illustrating an offset value setting method of the image measuring instrument.

An offset value $L_0$ is regularly set in ST4 as shown in FIG. 5. An offset value $L_0$ setting step (hereinafter referred to as ST4) includes ST41 to ST44.

In a brightness information acquiring step (hereinafter referred to as ST41), a reference gauge G is measured to acquire the test brightness $B_{TEST}$.

In a brightness information evaluation step (hereinafter referred to as ST42), when the difference between the reference brightness $B_{REF}$ and the acquired test brightness $B_{TEST}$ ($B_{REF}-B_{TEST}$) is larger than a threshold α, the processing proceeds to ST43. When the difference is less than the threshold α, the processing proceeds to ST44.

In a offset value changing step (hereinafter referred to as ST43), an appropriate value is assigned to an adjustment offset value $L_{0(ADJ)}$ for adjusting the offset value to substitute the adjustment offset value $L_{0(ADJ)}$ into the offset value $L_0$ to proceed to ST41. A flow from ST41 to ST43 is repeated so that the difference is less than the threshold α to proceed to ST44. Consequently, the offset value $L_{0(ADJ)}$ is automatically decided at which the difference less than the threshold α.

In an offset value storing step (hereinafter referred to as ST44), the offset value $L_0$ which is substituted by the adjustment offset value $L_{0(ADJ)}$ is updated.

In ST4 as described above, the offset value $L_0$ is set so that quantity of illumination light irradiated from the light source 17 on reception of a command signal based on the same illumination preset value $L_p$ remains the same before and after a state of the light source 17 is changed.

Advantages of Exemplary Embodiment

The exemplary embodiment offers the following advantages.

(1) Even when illumination light quantity of the light source 17 is changed, such as when the light source 17 deteriorates with the passage of time or when the light source 17 is replaced, the offset value $L_0$ can be easily set so that illumination light quantity remains the same after and before the change without modifying a preset illumination preset value $L_p$ for each of the measured points W1 to W3.

(2) A desired offset value $L_0$ can be obtained only by setting a predetermined threshold α and judging whether a difference in brightness information B of the illumination light quantity before and after the change of the state of the light source 17 ($B_{REF}-B_{TEST}$) is less than the threshold α. The offset value $L_0$ can be automatically set by a program for setting the offset value $L_0$ as described above.

(3) The brightness information B of the illumination light quantity before and after the state of the light source 17 is changed can be accurately detected by the reference gauge G, so that the change in the illumination light quantity obtained by the set offset value $L_0$ can be reduced.

MODIFICATION OF THE INVENTION

It should be noted that the invention is not limited to the above-described embodiment, and may be modified or improved as long as an object of the invention can be achieved.

For example, though the offset value assigner 41 and the offset value setting unit 42 are provided within the control unit 21 in the exemplary embodiment, an arrangement of the offset value assigner 41 and the offset value setting unit 42 is not limited thereto. The offset value assigner 41 and the offset value setting unit 42 may be provided in the illumination unit 19. Thus, by replacing a conventional illumination unit with the illumination unit 19 having an arrangement of the invention, parts to be modified of the conventional control unit 21 can be reduced, so that the setting method of the invention can be easily applied to an conventional image measuring instrument.

The setting method of the invention is applicable to a transmitted illumination or ring illumination in place of an epi-illumination. For the transmitted illumination, an optically transmissive to-be-measured object mounting unit is provided in the center of the stage 11. A to-be-measured object W may be mounted on an upper surface of the mounting unit, and a light source for the transmitted illumination is provided on a lower position. For the ring illumination, a light source for the ring illumination, which irradiates light from obliquely above a to-be-measured object W.

Though the offset value $L_0$ is automatically set by the reference gauge G in the exemplary embodiment, the setting method is not limited thereto. The offset value $L_0$ may be manually set using the to-be-measured object W.

Also, the assigned offset value $L_0$ can be changed in accordance with the duration of the use of the light source 17. At this time, the offset value $L_0$ may be inputted by the input unit. Alternatively, a relationship between the duration of use and the offset value $L_0$ may be preliminary stored as a chart data to update the offset value $L_0$ by reading the chart data as necessary.

The priority application Number JP2008-004650 upon which this patent application is based is hereby incorporated by reference.

What is claimed is:

1. An illumination light quantity setting method in an image measuring instrument including an image pickup that images a plurality of measured points based on a preset measuring procedure, and an illuminator that irradiates the measured points with light having illumination light quantity corresponding to a provided command signal, the image measuring instrument measuring a dimension and a shape of a to-be-measured object while the illuminator irradiates the measured points with light having illumination light quantity corresponding to an illumination preset value with reference to the illumination preset value that is preliminarily set and stored for each of the measured points, the setting method comprising:
    a command signal output step that outputs the command signal for irradiating light having the illumination light quantity corresponding to the illumination preset value for each of the measured points;
    an offset value assigning step that assigns an offset value to the command signal to be sent to the illuminator, the offset value being a common value, and the command signal being applicable to all of the measured points; and
    a setting step that sets the offset value to be variable without modifying the illumination preset value for every measured point.

2. The illumination light quantity setting method in the image measuring instrument according to claim 1, wherein
    in the setting step,
    a reference brightness information of an illumination light irradiated from the illuminator corresponding to the command signal is detected and stored,
    after the reference brightness information is detected, a brightness information of the illumination light irradiated from the illuminator corresponding to the command signal is detected to be compared with the reference brightness information, and
    the offset value is changed when a variation of the brightness information relative to the reference brightness information is out of a predetermined range.

3. The illumination light quantity setting method in the image measuring instrument according to claim 2, wherein
    in the setting step,
    the illumination light is irradiated on a reference gauge to detect the reference brightness information and the brightness information.

4. An image measuring instrument including an image pickup that images a plurality of measured points based on a preset measuring procedure, and an illuminator that irradiates the measured points with light having illumination light quantity in accordance with a provided command signal, the image measuring instrument measuring a dimension and a shape of a to-be-measured object while the illuminator irradiates the measured points with light having illumination light quantity corresponding to an illumination preset value with reference to the illumination preset value that is preliminarily set and stored for each of the measured points, the image measuring instrument comprising:
    a command signal output unit that outputs a command signal for irradiating light having the illumination light quantity corresponding to the illumination preset value for each of the measured points;
    an offset value assigning unit that assigns an offset value to the command signal to be sent to the illuminator, the offset value being a common value, and the command signal being applicable to all of the measured points; and
    a setting unit that sets the offset value to be variable without modifying the illumination preset value for every measured point.

5. The illumination light quantity setting method in the image measuring instrument according to claim 1, wherein
    in the setting step,
    the offset value is preliminarily stored so as to be automatically updated according to a duration of use.

* * * * *